United States Patent
Pu et al.

(10) Patent No.: US 9,079,026 B2
(45) Date of Patent: Jul. 14, 2015

(54) PARTICLE BEAM SCANNING IRRADIATION SYSTEM

(75) Inventors: Yuehu Pu, Tokyo (JP); Masahiro Ikeda, Tokyo (JP); Taizo Honda, Tokyo (JP)

(73) Assignee: MITSUBISHI ELECTRIC CORPORATION, Chiyoda-Ku, Tokyo (JP)

( * ) Notice: Subject to any disclaimer, the term of this patent is extended or adjusted under 35 U.S.C. 154(b) by 0 days.

(21) Appl. No.: 14/386,626

(22) PCT Filed: Mar. 21, 2012

(86) PCT No.: PCT/JP2012/057182
§ 371 (c)(1),
(2), (4) Date: Sep. 19, 2014

(87) PCT Pub. No.: WO2013/140547
PCT Pub. Date: Sep. 26, 2013

(65) Prior Publication Data
US 2015/0038766 A1  Feb. 5, 2015

(51) Int. Cl.
*A61N 5/10* (2006.01)
(52) U.S. Cl.
CPC .............. *A61N 5/1071* (2013.01); *A61N 5/103* (2013.01); *A61N 5/1031* (2013.01); *A61N 5/1043* (2013.01); *A61N 2005/1087* (2013.01)
(58) Field of Classification Search
USPC ........................................................ 250/492.3
See application file for complete search history.

(56) References Cited

U.S. PATENT DOCUMENTS 7,102,144 B2 * 9/2006 Matsuda et al. ........... 250/492.1
2006/0102856 A1 5/2006 Matsuda et al.
(Continued)

FOREIGN PATENT DOCUMENTS

JP 2006-145213 A 6/2006
JP 2008-136523 A 6/2008
(Continued)

OTHER PUBLICATIONS

International Search Report (PCT/ISA/210) mailed on Jun. 5, 2012, by the Japanese Patent Office as the International Searching Authority for International Application No. PCT/JP2012/057182.
(Continued)

*Primary Examiner* — Kiet T Nguyen
(74) *Attorney, Agent, or Firm* — Buchanan Ingersoll & Rooney PC

(57) ABSTRACT

A particle beam scanning irradiation method includes the steps of calculating a planned irradiating particle count of a particle beam for each of irradiation spots, on the basis of a relative amount of particle beam irradiation and a prescription particle-beam dose determined from a particle-beam therapy plan; simulating an irradiation process of the particle beam at each irradiation spot, on the basis of the planned irradiating particle count and a beam current waveform of the particle beam, and calculating a particle count of the particle beam irradiating the diseased portion during a scan shift of the particle beam; correcting the planned irradiating particle count for each irradiation spot by using the irradiating particle count during the scan shift; converting the corrected planned-irradiation particle count into a count value used in a dose monitor; and irradiating the irradiation spot with the particle beam, on the basis of the converted count value.

5 Claims, 7 Drawing Sheets

(56) References Cited

U.S. PATENT DOCUMENTS

2012/0001085 A1     1/2012    Fujimoto et al.
2014/0046113 A1     2/2014    Fujimoto et al.

FOREIGN PATENT DOCUMENTS

| | | |
|---|---|---|
| JP | 2009-066106 A | 4/2009 |
| JP | 2010-251106 A | 11/2010 |
| JP | 2011-156340 A | 8/2011 |
| JP | 2012-010821 A | 1/2012 |

OTHER PUBLICATIONS

T. Inaniwa et al., "Optimization for fast-scanning irradiation in particle therapy", Medical Physics, Aug. 2007, pp. 3302-3311, vol. 34, No. 8.

Japanese Office Action dated Feb. 3, 2015 issued in corresponding Japanese Patent Appl. No. 2014-505878, with English translation (5 pages).

Partial Translation of Japanese Office Action dated Feb. 3, 2015 issued in corresponding Japanese Patent Appl. No. 2014-505878 (3 pages).

\* cited by examiner

PARTICLE BEAM SCANNING IRRADIATION SYSTEM

TECHNICAL FIELD

The present invention relates to a particle beam therapy apparatus, more particularly to a particle beam scanning irradiation system for irradiating a diseased portion with a particle beam in accordance with its three-dimensional shape.

BACKGROUND ART

In a particle beam therapy, a diseased portion is irradiated with, for example, a proton beam or a carbon beam accelerated up to 70% of the light velocity. Such a high-energy particle beam has the following characteristics when irradiating into a tumor or the like in a body. Firstly, an irradiating particle beam stops almost at a penetration position proportional to the particle beam energy raised to the 1.7th power. Secondly, the energy density that is imparted to the path through which the irradiating particle beam penetrates until it stops in a body becomes maximum at the particle beam stop position. The energy density of the particle beam is referred to as a dose. A characteristic depth dose profile formed along the path through which a particle beam penetrates into a body is referred to as "Bragg curve".

The position where the dose of the particle beam becomes a maximum value is referred to as "Bragg peak". The particle beam scanning irradiation system scans a tumor so that the Bragg peak position is kept coincident with its three-dimensional shape. A peak dose at each scanning position is adjusted to form a three-dimensional dose distribution in a target (tumor portion) determined preliminarily by an imaging diagnosis.

A method of scanning irradiation positions with a particle beam includes a scanning method in the lateral directions (X- and Y-directions) substantially orthogonal to the irradiation direction of the particle beam and a scanning method in the depth direction (Z-direction) being the irradiation direction of the particle beam. In the lateral scanning, there are a method of moving a patient with respect to the particle beam and a method of shifting the position of the particle beam using an electromagnet or the like. The latter method using an electromagnet is generally employed.

Varying energy of the particle beam is only method for scanning in the depth direction. Two methods are conceivable for the energy variation: a method of varying the particle beam energy by an accelerator and a method of using an energy varying device called a range shifter installed in a beam delivery line or an irradiation line. Nowadays, the method using an energy varying device is widely employed. A range shifter may sometimes include a device called an energy selection system that performs energy analysis and momentum selection.

The method for lateral scanning of a particle beam is classified into two basic irradiation methods: a spot scanning irradiation method and a hybrid scanning irradiation method. In a spot scanning irradiation method, a particle beam is emitted and intensity of the particle beam is once weakened when an irradiation amount at a given irradiation position reaches a planned value (refer to Non-Patent Document 1). At this time, the particle beam intensity is generally set to zero. To irradiate a next irradiation position with the particle beam, a current value for the scanning electromagnet is changed and the particle beam intensity is increased again, and then the particle beam is emitted. Instead of increasing the particle beam intensity, re-extraction of the particle beam from the accelerator is also made.

In the hybrid scanning irradiation method, while its basic way of irradiating a planned position with the particle beam by a planned amount is the same as with the spot scanning irradiation method, the particle beam is scanned not with the irradiation being stopped but with the irradiation being continued when shifted to a next irradiation position (refer to Non-Patent Document 1).

PRIOR ART DOCUMENT

Patent Document

Patent Document 1: JP 2006-145213 A
Patent Document 2: JP 2008-136523 A
Patent Document 3: JP 2011-156340 A Non-Patent Document Non-Patent Document 1: T. Inaniwa, et al, Medical Physics, 34, 2007, p. 3302

SUMMARY OF THE INVENTION

Problem that the Invention is to Solve

In a particle beam scanning irradiation system, the particle beam is shifted while an irradiation position is being changed. A dose during the shift of the particle beam influences a dose distribution in an actual irradiation. In Non-Patent Document 1, by incorporating contribution of a dose during the particle beam shift into an optimum calculation of the therapy planning, influence of the in-shift dose to a final dose distribution is reduced. This method needs preliminary determination of the in-shift dose contribution.

Since the contribution of the in-shift dose in an actual irradiation depends on time variation of intensity of the particle beam extracted from the accelerator during the particle beam irradiation, the method requires the incorporation of an average value of the in-shift dose contribution into the optimum calculation of the therapy planning. When a beam current waveform I(t) extracted from the accelerator varies largely with time, it is difficult to take the contribution of the in-shift particle beam into account with high accuracy. Furthermore, the average of the in-shift dose contribution needs to be taken into account in the optimum therapy-planning calculation. This relatively complicates creation of the therapy planning.

The present invention is made to resolve the above problems, and aims at reducing the difference between a dose distribution at an actual irradiation and a planned irradiating particle count at each of irradiation spots (irradiation positions) determined in accordance with a therapy plan.

Means for Solving the Problem

A particle beam scanning irradiation method according to the present invention includes a first step of calculating a planned irradiating particle count of a particle beam for each of irradiation spots, on the basis of a relative amount of particle beam irradiation and a prescription particle-beam dose that are determined from a particle-beam therapy plan; a second step of simulating an irradiation process of the particle beam at each irradiation spot, on the basis of the planned irradiating particle count and a beam current waveform of the particle beam, and of calculating a particle count of the particle beam irradiating the diseased portion during a scan shift of the particle beam; a third step of correcting the planned irradiating particle count for each irradiation spot by using the irradiating particle count during the scan shift; a fourth step of converting the corrected planned-irradiation particle count into a count value used in a dose monitor; and a fifth step of irradiating the irradiation spot with the particle beam, on the basis of the converted count value.

Advantages of the Invention

According to a particle beam scanning irradiation system of the present invention, a dose distribution at an actual irradiation can be approximated, with a simple correction method, to a planned irradiating particle count at each of irradiation spots (irradiation positions) determined in accordance with a therapy plan.

EMBODIMENTS FOR CARRYING OUT THE INVENTION

Embodiment 1

Figure 1:
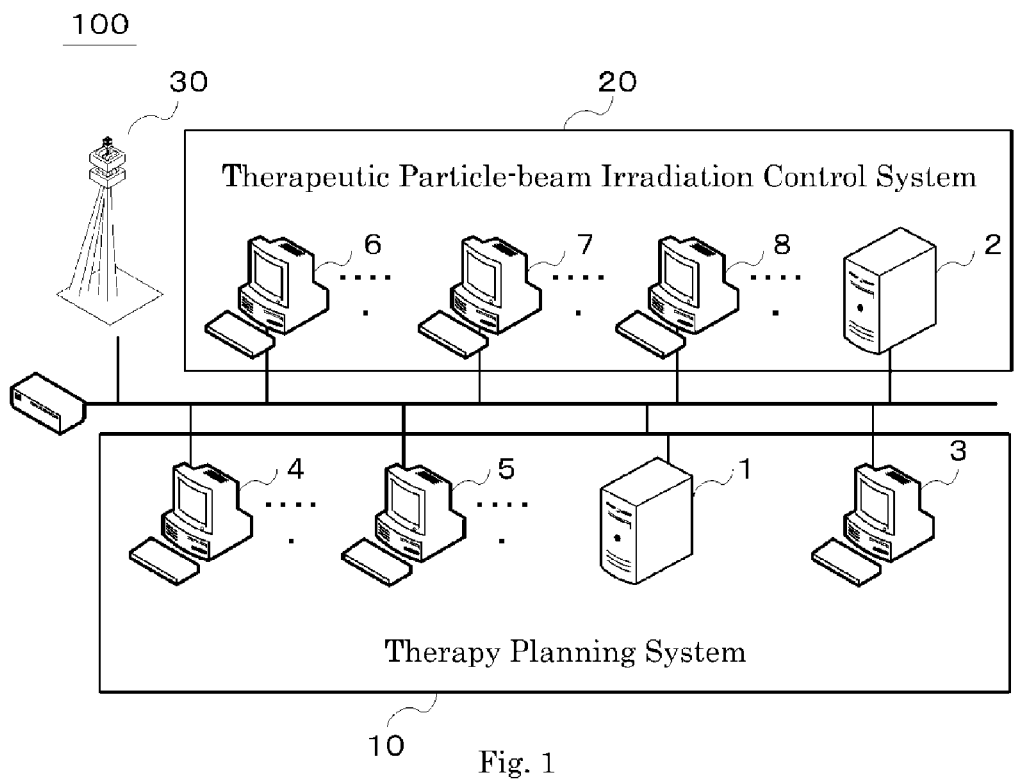
FIG. 1 is a diagram showing an overall configuration of a particle beam scanning irradiation system according to the present invention.

FIG. 1 shows an overall configuration of a particle beam scanning irradiation system. The particle beam scanning irradiation system 100 includes a therapy planning system 10, a therapeutic particle-beam irradiation control system 20, and a particle beam irradiation device 30. The therapy planning system 10 includes a therapeutic planned data management unit 1, a planned irradiating particle count correction unit 3, a therapy planning unit 4, a scanning irradiation simulation unit 5, and others. The therapeutic particle-beam irradiation control system 20 includes an irradiation data management unit 2, a therapeutic control unit 6, a component control unit 7, and a positioning unit 8. The therapeutic control unit 6 includes a dose monitor, and the particle beam irradiation device 30 includes a scanning magnet and a scanning power supply.

The therapy planning unit 4 is for creating a therapy plan and simulates a dose calculation on the basis of the therapy plan. The therapeutic control unit 6 controls the particle beam irradiation device 30 to emit the particle beam in accordance with conditions specified by the therapy plan acquired from the irradiation data management unit 2. An actual dose of the particle beam is measured by the therapeutic control unit 6. The measurement result is transmitted to the therapeutic planned data management unit 1. The therapeutic planned data management unit 1 manages data created by the planned irradiating particle count correction unit 3, the therapy planning unit 4, and the scanning irradiation simulation unit 5. The irradiation data management unit 2 manages data, therapy records, measurement records, and the like used in the therapeutic control unit 6, the component control unit 7, and the positioning unit 8.

Figure 2:
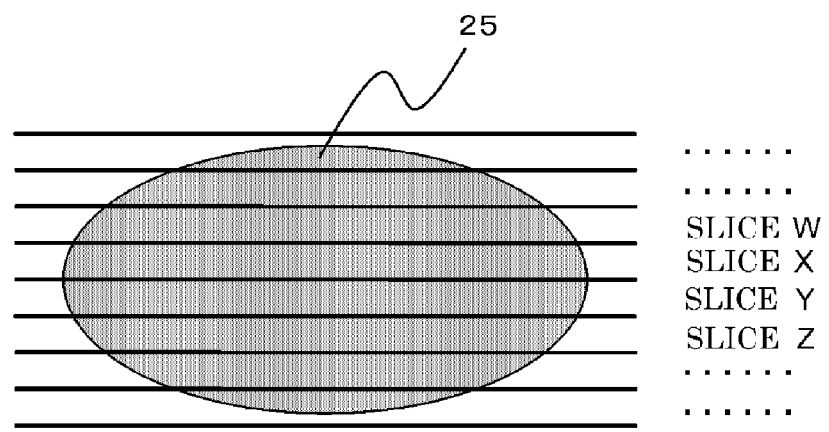
FIG. 2 is a diagram showing a sliced state of a diseased portion.

In a particle beam therapy, since a tumor is scanned so that the Bragg peak position is kept coincident with its three-dimensional shape, a diseased portion is cut into virtual thin slices in the depth direction in accordance with a therapy plan. FIG. 2 schematically shows a sliced diseased portion 25 such as a tumor. One layer of the diseased portion 25 divided in the depth direction is called a slice. The diseased portion 25 is divided into a plurality of slices ( . . . , W, X, Y, Z, . . . ).

Figure 3:
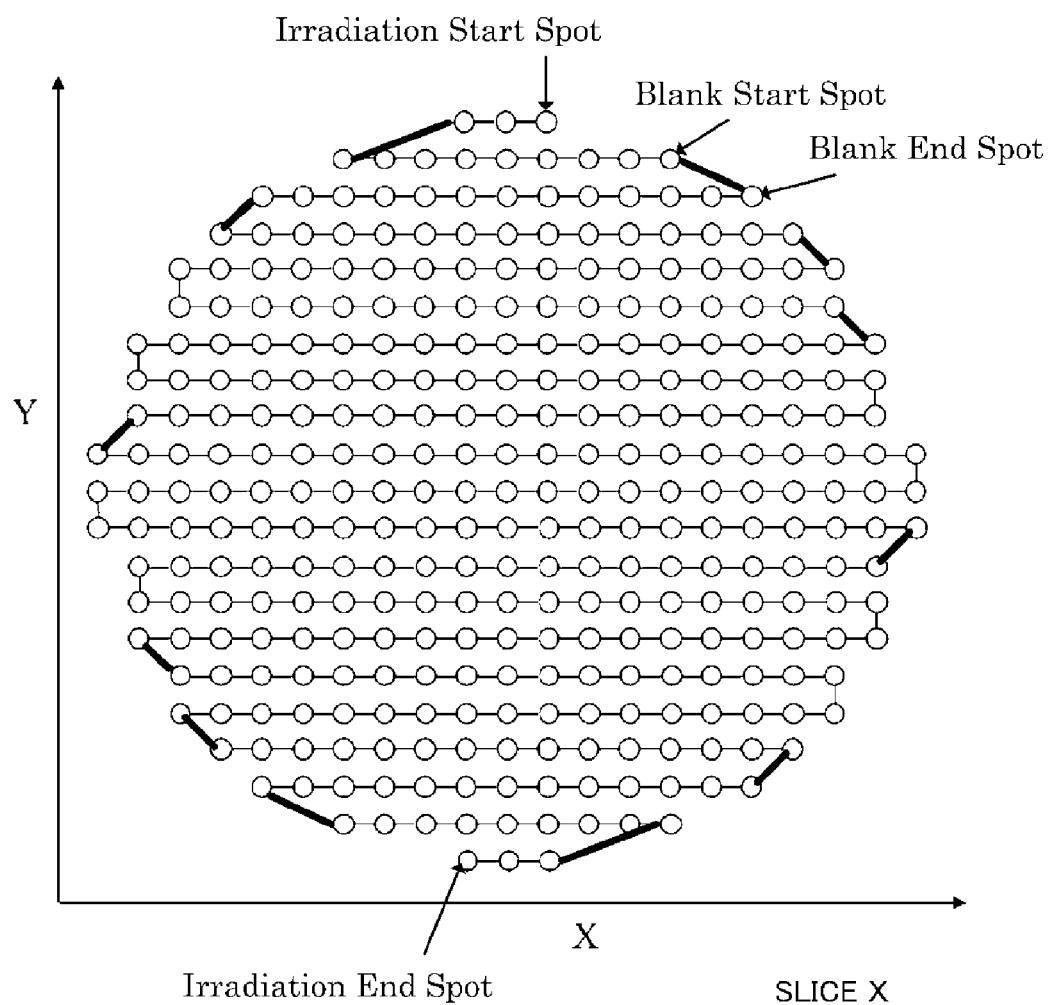
FIG. 3 is a diagram showing positional relationship between an irradiation start spot and an irradiation end spot.

Next, the order of the particle beam irradiation in a scanning irradiation is described with reference to FIG. 3. The irradiation order of the particle beam is preliminarily calculated by the therapy planning system 10. An arrangement of irradiation spots and a scanning pathway of the particle beam in a given slice X are illustrated in the figure. The particle beam traces in a single stroke writing manner in principle from a start spot of the irradiation to an end spot of the irradiation. The particle beam ordinarily moves with a scan shift to an adjoining irradiation spot. When irradiation spots are distant, the particle beam moves with a blank shift to next irradiation spot to skip between the irradiation spots. The number of spots that are omitted from the irradiation by the blank shift is different depends on irradiation conditions. The blank shift is started from a blank start spot and ended at a blank end spot.

Figure 4:
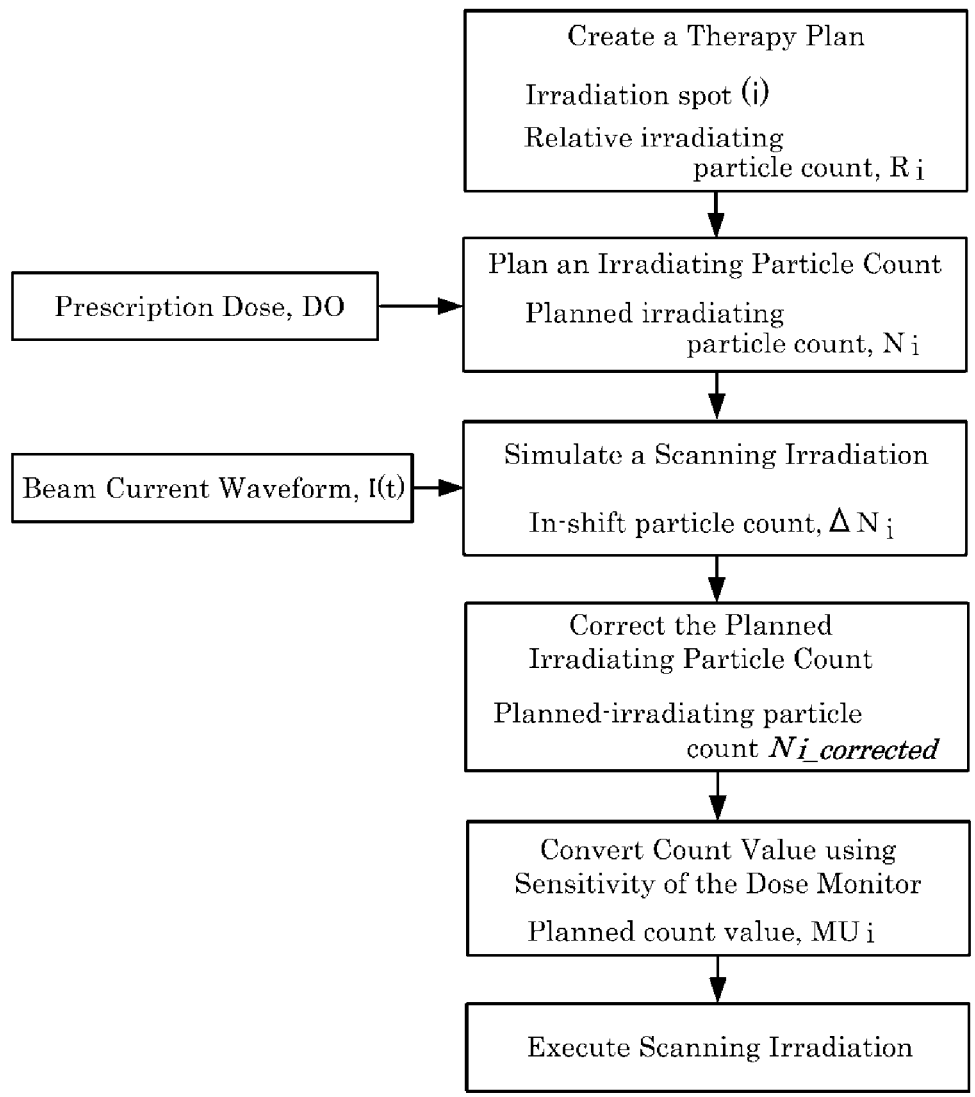
FIG. 4 is a flow diagram showing a process of a particle beam scanning irradiation method according to Embodiment 1 of the present invention.

Next, a particle beam scanning irradiation method according to Embodiment 1 of the present invention is described with reference to the flow diagram shown in FIG. 4. A planned irradiating particle count $N_i$ indicates a planned value (prescription particle count) determined by the therapy plan for an irradiation spot (i), where a spot number i (=1, 2, 3, . . . , $N_{spot}$) represents an identity (ID) of the irradiation spot. Spots in the same slice are irradiated with the particle beam in the order of the spot number i. The planned irradiating particle count $N_i$ is determined on the basis of the therapy plan. The planned irradiating particle count $N_i$, which is stored in the therapeutic planned data management unit 1, is calculated from a prescription dose DO and a relative irradiating particle count $R_i$ output for each spot from the therapy planning system 10. The prescription dose DO represents a dose of the particle beam irradiating a diseased portion at one time.

Figure 5:
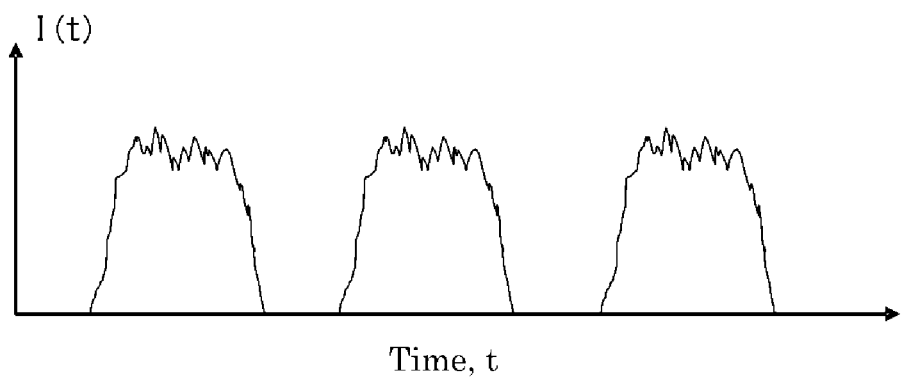
FIG. 5 is a graph showing a beam current waveform used in a scanning irradiation simulation according to Embodiment 1 of the present invention.

A beam current waveform I(t) is stored in the irradiation data management unit 2 and updated day by day on an as-needed basis to reflect a latest measurement result. FIG. 5 shows an example of the beam current waveform I(t) used at the scanning irradiation. The beam current waveform I(t) is basic time-varying information on beam current of the particle beam extracted from the accelerator. Note that regarding an accelerator used in the scanning irradiation, any type of accelerator such as a synchrotron accelerator or a cyclotron accelerator is available alike to the present invention. The scanning irradiation simulation unit 5 calculates estimation data concerning the number of particles that irradiate the diseased portion during a beam shift between spots. The planned irradiating particle count $N_i$ is corrected by the planned irradiating particle count correction unit 3. The therapy plan includes a therapeutic scanning irradiation plan. The planned irradiating particle count $N_i$ being corrected is converted into a count value MU (monitor unit) so as to adapt to the dose monitor.

An operation of the particle beam scanning irradiation system 100 according to Embodiment 1 of the present invention will be described next with reference to FIGS. 1 through 4. First, a therapeutic scanning irradiation plan is created on the basis of computer tomography (CT) data and the like of a patient by means of the therapy planning system 10. As a result, an irradiation direction of the particle beam, irradiation slice information corresponding to the irradiation direction, irradiation position information for each slice, and relative irradiation dose information for an irradiation spot at each irradiation position are output. A case of a plurality of irradiation directions is also conceivable. An irradiation spot is defined in the irradiation position information in correspondence with an irradiating position.

Next, the therapy planning unit 4 calculates the planned irradiating particle count $N_i$ on the basis of the prescription dose DO and the therapy plan. For the calculation of the planned irradiating particle count $N_i$, the relative irradiating particle count for each spot included in the therapy plan and measurement information on an absolute value of a dose distribution in water are utilized. The planned irradiating particle count $N_i$ and the beam current waveform I(t) for each irradiation spot are input to the scanning irradiation simulation unit 5.

The scanning irradiation simulation unit 5 is constituted with simulation software and a computer. When the scanning irradiation is carried out, the scanning irradiation simulation unit 5 calculates a beam particle count $\Delta N_i$ (i=1, 2, 3, . . . , $N_{spot-1}$) irradiating the diseased portion while the particle beam is shifting from an irradiation spot (i) to the irradiation spot (i+1). The simulation of the scanning irradiation process takes into account the time responses and the operations of the dose monitor, the scanning power supply, a scanning controller, and the like.

The scanning irradiation simulation unit 5 integrates the beam current waveform I(t) in intervals of several microseconds. When the current integral value reaches the planned irradiating particle count $N_i$ for an irradiation spot (i), the irradiation position of the particle beam is changed to the irradiation spot (1+1) taking response times of the various components into account. The beam current waveform I(t) is integrated further for the irradiation spot (1+1), and when the current integral value reaches the planned irradiating particle count $N_{i+i}$, the irradiation position is changed to the irradiation spot (1+2). In this way, by simulating the process of irradiating with the particle all irradiation spots beam from the irradiation spot (i=1) to the irradiation spot (i=$N_{spot}$), a beam particle count (in-shift particle count $\Delta N_i$) irradiating the diseased portion while the beam shifts between the irradiation spots can be calculated. The in-shift particle count $\Delta N_1$ is not taken into account in calculating the planned irradiating particle count $N_i$. In actual irradiation, however, since the beam starts shifting after an irradiating particle count reaches the planned irradiating particle count $N_i$, the diseased portion is irradiated excessively with the particle beam until the particle beam shifts the next irradiation spot (see FIG. 7).

Next, the planned irradiating particle count correction unit 3 corrects the planned irradiating particle count $N_i$ for an irradiation spot (i) using the in-shift particle count $\Delta N_i$. The in-shift particle count $\Delta N_i$ is an irradiating particle count during the shift between the irradiation spots (i) and the irradiation spot (i+1). Specifically, a corrected planned-irradiating particle count $N_{i\_corrected}$ (=$N_i$−$\Delta N_i$/2) and a corrected planned-irradiating particle count $N_{i+1\_corrected}$ (=$N_{i+1}$−$\Delta N_i$/2) are calculated. This calculation determines the corrected planned-irradiating particle count $N_{i\_corrected}$. The corrected planned-irradiating particle count $N_{i\_corrected}$ is a planned irradiating particle count that takes into account the effect of a particle count irradiating during the shift between spots. Focusing on the irradiation spot (i), the following equation holds true (see FIG. 7).

$$N_{i\_corrected}=N_i-\Delta N_i/2-\Delta N_{i-1}/2$$

Note that an in-shift particle count $\Delta N_{i-1}$ is a particle count irradiating during the shift between the irradiation spots (i−1) and (i) (1<i<$N_{spot}$). The correction equations for the irradiation spots (1) and ($N_{spot}$) change to $N_i$−$\Delta N_i$/2 and $N_{i-1}$−$\Delta N_{i-1}$/2, respectively.

The corrected planned-irradiating particle count $N_{i\_corrected}$ is converted into a planned count value $MU_i$ using sensitivity of the dose monitor managing (or measuring) a particle count during irradiation. The dose monitor sensitivity depends on the particle beam energy. Finally, the planned count value $MU_1$ obtained for each spot is sent to the therapeutic particle-beam irradiation control system 20 and the particle beam irradiation device 30 to perform an actual scanning irradiation. In performing the actual scanning irradiation using the therapeutic particle-beam irradiation control system 20, an accelerator beam is used that has the same intensity and basic time pattern as that used in simulating a scanning irradiation by the scanning irradiation simulation unit 5.

Figure 7:
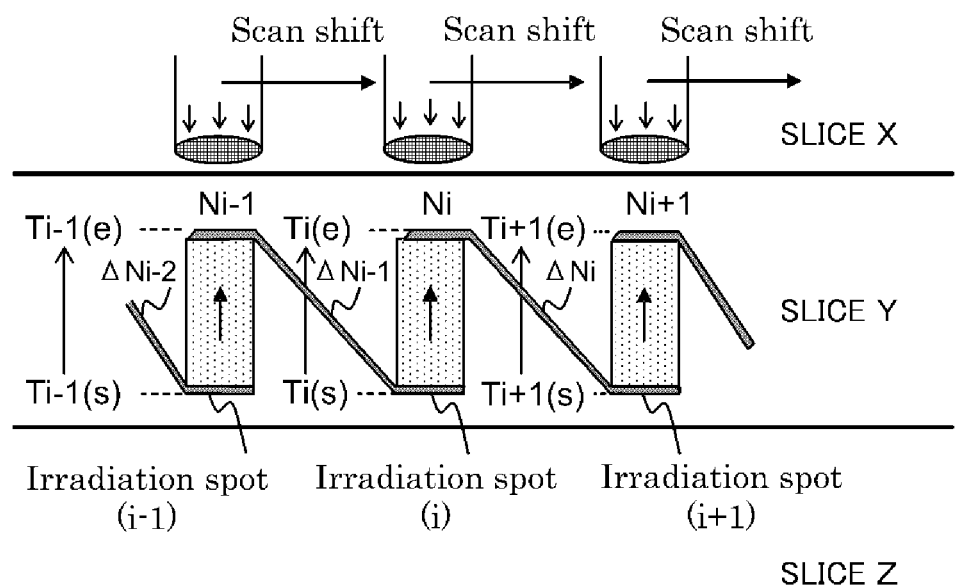
FIG. 7 is a diagram for explaining movement of the particle beam spot.

The amount of particle beam actually irradiating the irradiation spot (i) is controlled on the basis of the planned count value $MU_i$. FIG. 7 schematically shows how the particle beam irradiating a slice Y is counted. The beam shifts along the irradiation spots in the order of . . . , (i−1), (i), (i+1), . . . . The irradiating particle beam is counted in one cycle from a start point $T_{i(s)}$ to an end point $T_{i(e)}$. This counting cycle is continuously repeated. In actual irradiation, when the counting starts, the irradiation is continued by the in-shift particle beam from the preceding cycle. When the counting ends, the particle beam starts shifting toward the next irradiation spot.

As has been described above, a particle beam scanning irradiation system described in Embodiment 1 of the present invention takes into account, at the scanning irradiation, influence of the in-shift particle beam to the dose distribution of a target irradiated during the shift between spots. The in-shift particle count $\Delta N_i$ is calculated before irradiation by using the scanning irradiation simulation unit capable of simulating an actual irradiation timing and the corrected planned-irradiating particle count $N_{i\_corrected}$ is calculated by using the planned irradiating particle count correction unit, and then an actual scanning irradiation is performed. This eliminates re-plan processing by the therapy planning system. As a result, a therapy plan for particle beam scanning irradiation can be simplified, thus improving operation efficiency of the particle beam scanning irradiation system. Moreover, the scanning irradiation can be performed taking the influence of the in-shift particle beam into account, giving a higher accurate dose to a diseased portion.

Embodiment 2

An operation of the particle beam scanning irradiation system is described next according to Embodiment 2 of the present invention. Embodiment 2 has a feature in that a beam current waveform whose fast fluctuation components are removed as shown in FIG. 6 is used as a beam current waveform I(t) in the scanning irradiation simulation unit 5, instead of an actually measured beam current waveform shown in FIG. 5.

Figure 6:
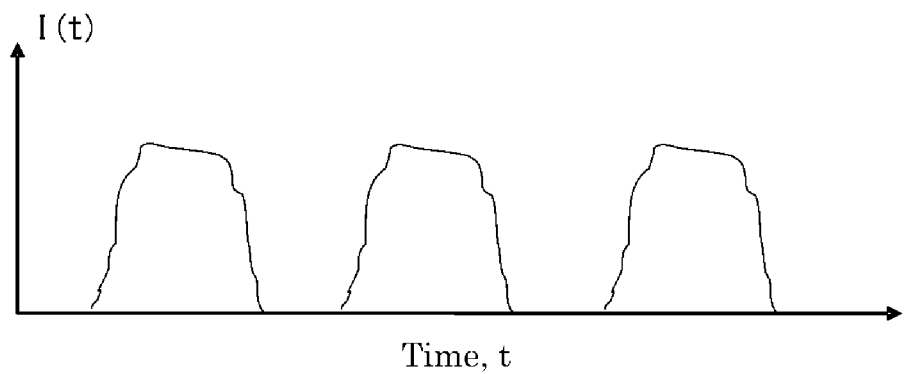
FIG. 6 is a graph showing a smoothed beam current waveform used in a scanning irradiation simulation according to Embodiment 2 of the present invention.

The beam current waveform I(t) shown in FIG. 6 is obtained by smoothing the beam current waveform I(t) shown in FIG. 5 through a low-pass filter. By the smoothing, an in-shift particle count $\Delta N_i$ during a shift between spots can be determined as a more stable averaged value of the beam current waveform. This eliminates influence of the poorly-reproducible and fast varying beam current and allows for determining the in-shift particle count $\Delta N_i$ with higher accuracy. The particle beam scanning irradiation system according to Embodiment 2 brings about an effect of irradiating, with higher accuracy, a diseased portion with the particle beam.

Embodiment 3

Figure 8:
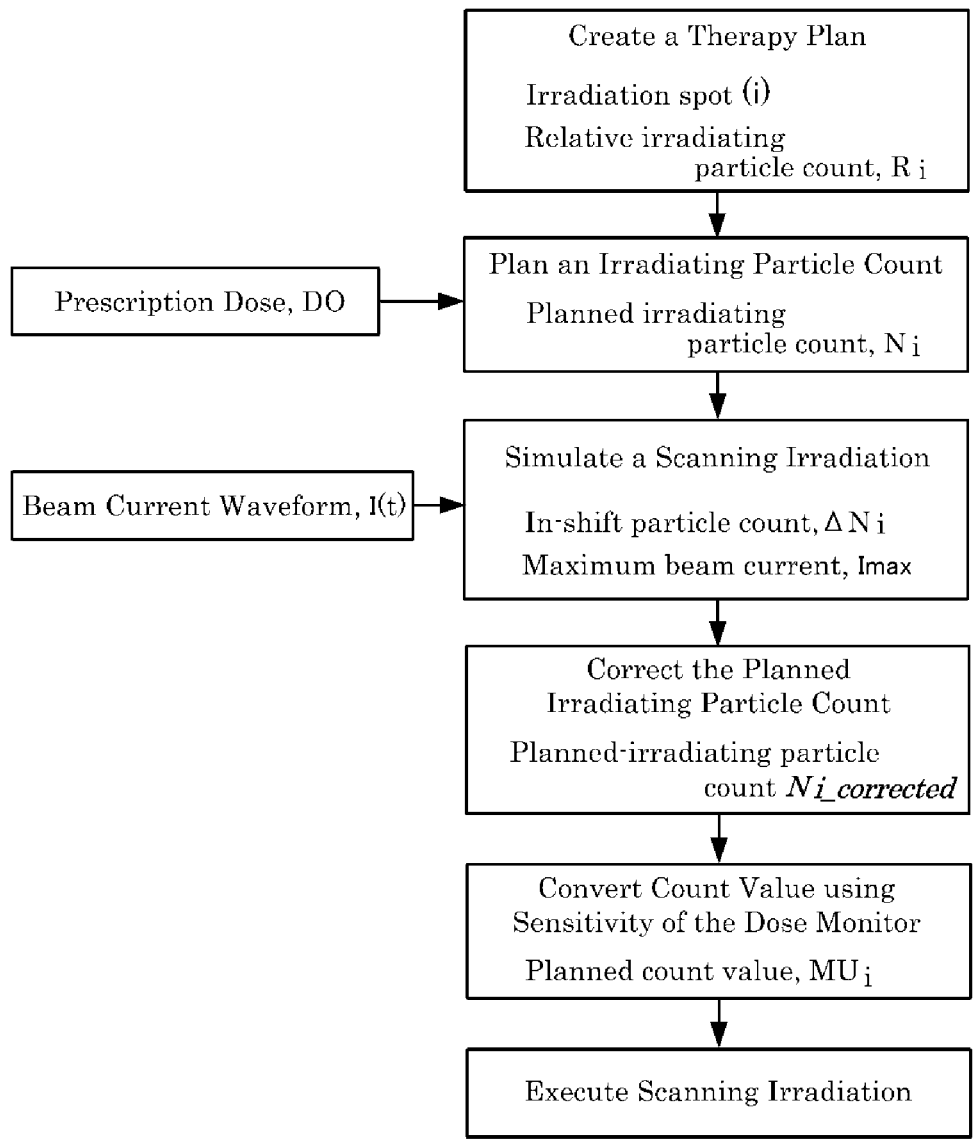
FIG. 8 is a flow diagram showing a process of a particle beam scanning irradiation method according to Embodiment 3 of the present invention.

An operation of the particle beam scanning irradiation system is described next according to Embodiment 3 of the present invention. While a large beam current can cause irradiation time to shorten, it is conceivable that a corrected planned-irradiating particle count $N_{i\_corrected}$ becomes negative because an in-shift particle count $\Delta N_i$ accounts for a relatively large percentage. FIG. 8 is a flow diagram showing a process of a particle beam scanning irradiation method according to Embodiment 3 of the present invention. The same symbols used in FIG. 8 as those in FIG. 4 represent in principle the same meaning as FIG. 4.

In Embodiment 3, in order to prevent a corrected planned-irradiating particle count $N_{i\_corrected}$ from becoming negative, a maximum beam current used in irradiating each slice is limited so that half an in-shift particle count $\Delta N_i$ is smaller than planned irradiating particle counts for spots before and after a beam shift. Because a waveform of the beam current is substantially the same, the same limitation holds also for the case of using an averaged value of the smoothed beam current.

To be specific, a maximum value of the beam current waveform IN (a maximum beam current at a certain time), which is used for irradiation of each slice, is preliminarily determined in the simulation of the scanning irradiation so that half ($\Delta N_i/2$) an in-shift particle count $\Delta N_i$ does not exceed a planned irradiating particle count $N_i$ for an irradiation spot (i) and a planned irradiating particle count $N_{i+1}$ for the irradiation spot (i+1). In irradiating a slice, while using a larger beam current can cause irradiation time to shorten, it is better, as a guideline, to irradiate the slice with a beam current equal to or less than half the maximum beam current calculated here.

In Embodiment 3, since a preliminarily limited maximum value of the beam current is used in irradiating each slice, a range of the beam current used in irradiating each slice can be properly set. This eliminates a corrected planned-irradiating particle count $N_{i\_corrected}$ to become negative and ensures it to be always positive in correcting a planned irradiation particle count. Consequently, the particle beam scanning irradiation can be performed with higher accuracy taking the influence of error in the particle count into account, in comparison with a case of performing irradiation with a negative particle count being set to zero.

Embodiment 4

Figure 9:
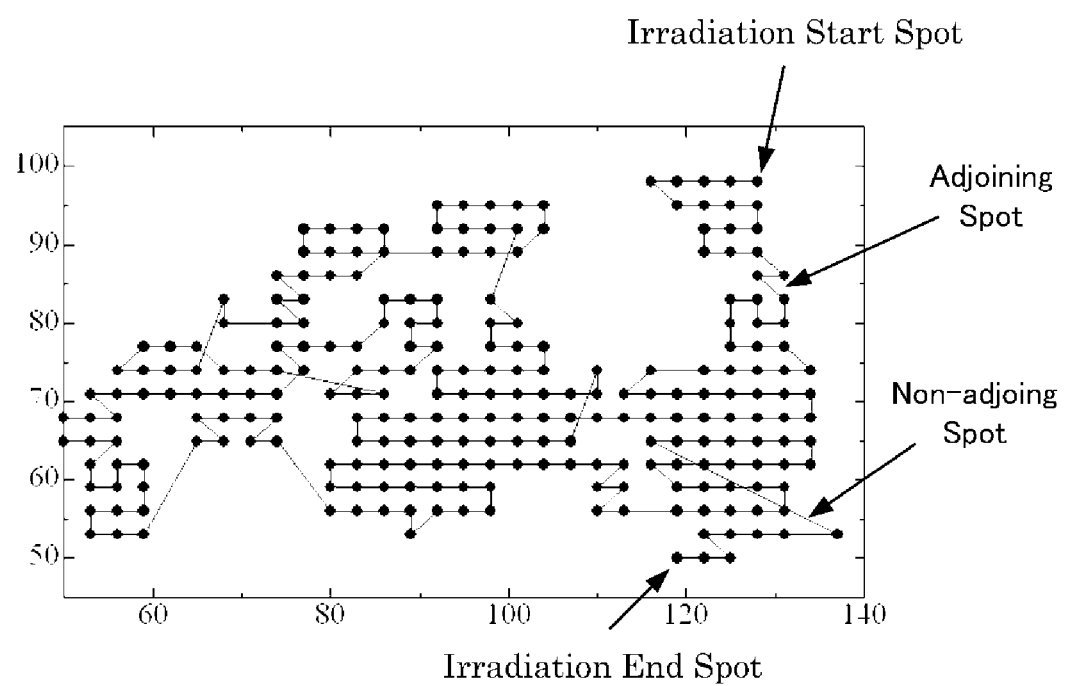
FIG. 9 is a diagram for explaining particle-beam scanning-irradiation system operations according to Embodiment 4 and Embodiment 5 of the present invention.

An operation of the particle beam scanning irradiation system is described next according to Embodiment 4 of the present invention. FIG. 9 shows an arrangement of irradiation spots and a scanning pathway in a given slice when a diseased portion is cut into virtual slices in its depth direction to be scanning-irradiated. A scanning irradiation starts at a spot in the uppermost right side and ends at a spot in the lowermost right side. In the midway between the irradiation start spot and the irradiation end spot, each spots in the slice is irradiated along a complicated pathway. In the figure, there are spot-to-spot shifts connecting between adjoining spots and spot-to-spot shifts connecting between non-adjoining spots.

In Embodiment 4, attention is focused on a spot-to-spot shift connecting between adjoining irradiation spots and a spot-to-spot shift connecting between non-adjoining irradiation spots. In the case of the shift between adjoining spots, the correction is made as described in Embodiment 1. When a shift occurs between non-adjoining spots, however, the correction method according to Embodiment 1 leads a large error. For that reason, in Embodiment 4, the planned irradiating particle count correction unit 3 preliminarily checks whether a shift is between spots or between non-adjoining spots. Only for a shift between adjoining spots, performed is the correction calculations of subtracting half the in-shift particle count $\Delta N_i$ from the planned irradiating particle count $N_i$ for an irradiation spot (i) before the shift and from the planned irradiating particle count $N_{i+1}$ for the irradiation spot (i+1) after the shift.

According to Embodiment 4, the correction calculation of subtracting half the in-shift particle count $\Delta N_1$ from the planned irradiation particle count $N_i$ is performed only when the particle beam shifts between adjoining spots. Since no correction is made when the particle beam shifts between non-adjoining spots, an error due to the correction calculation does not occur. In practice, the case when the particle beam shifts between non-adjoining spots much less occurs than the case when the particle beam shifts between adjoining spots. The case-by-case correction calculation achieves the scanning irradiation with higher accuracy.

Embodiment 5

An operation of the particle beam scanning irradiation system is described next according to Embodiment 5 of the present invention. In Embodiment 5, the particle beam scanning irradiation system performs, using the planned irradiating particle count correction unit 3, different planned irradiating particle count correction calculations for the respective cases of shifting between adjoining spots (scan shift) and of shifting between non-adjoining spots (blank shift) shown in FIG. 9. Specifically, for the case of shifting between adjoining spots, performed are the correction calculations of subtracting half the in-shift particle count $\Delta N_i$ from the planned irradiating particle count $N_i$ for an irradiation spot (i) before the shift and from the planned irradiating particle count $N_{i+1}$ for the irradiation spot (i+1) after the shift, as with Embodiment 1.

For the case of shifting between non-adjoining spots, a shift path is determined first. Then, all spots (i=ik, k=1, 2, 3, . . . , nk; where nk is the number of all spots, and i1=i, ink=i+1), which are substantially spot-size apart from each other, are determined from the determined shift-path. The number of spots determined is defined as the number of blank spots nk. Next, the in-shift particle count $\Delta N_i$ is divided by the number of blank spots nk, to perform respective corrections of subtracting $\Delta N_i/nk$ from a planned irradiating particle count N for the spot (i) before the shift, from that for the spot (i+1) after the shift, and from those for the blank spots involved in the shift.

According to the embodiment, an in-shift particle count can be corrected more accurately also for the case of shifting between non-adjoining spots. Therefore, accuracy of the scanning irradiation can be further increased in comparison with Embodiment 4. Note that, in the above embodiments, the scanning irradiation simulation unit, the therapy planning unit, and the planned irradiating particle count correction unit are shown and described as individual components. Actually, installing in one unit a computer code that represents the same functions of these units or installing on a computer the same functions as those of these units also brings about the same effects as those described above. This allows influence of a dose due to the in-shift particle beam to be taken into account with high accuracy using the simple method having been described above.

In the present invention, each embodiment may be freely combined, and/or appropriately modified and/or omitted within the scope and spirit of the invention.

REFERENCE NUMERALS

1: treatment plan data management unit, 2: irradiation data management unit, 3: planned irradiating particle count correction unit, 4: therapy planning unit, 6: therapeutic control unit, 10: therapy planning system, 20: therapeutic particle-beam irradiation control system, 30: particle beam irradiation device, 100: particle beam scanning irradiation system

The invention claimed is:

1. A particle beam scanning irradiation system comprising:
a computer that calculates a planned irradiating particle count of a particle beam for each of a plurality of irradiation spots, on the basis of a particle-beam therapy plan; and
a particle beam irradiation device that irradiates a diseased portion with the particle beam, wherein
the computer simulates an irradiation process of the particle beam at each irradiation spot, on the basis of the planned irradiating particle count and a beam current waveform of the particle beam, and executes
a first step of calculating a particle count of the particle beam irradiating the diseased portion during a scan shift of the particle beam;
a second step of correcting the planned irradiating particle count for each irradiation spot by using the irradiating particle count during the scan shift, wherein the second step includes calculations of subtracting half the irradiating particle count during the scan shift from a planned irradiating particle count for an irradiation spot before the scan shift and from a planned irradiating particle count for an irradiation spot after the scan shift; and
a third step of converting the corrected planned-irradiating particle count into a count value used in a dose monitor, and
the particle beam irradiation device irradiates the diseased portion with the particle beam, on the basis of the count value converted in the third step.

2. The particle beam scanning irradiation system of claim 1, further including a fourth step of smoothing the particle beam current waveform to use the smoothed beam current waveform in the second step.

3. The particle beam scanning irradiation system of claim 1, further including a fifth step of setting, on the basis of the particle beam current waveform, a magnitude of the beam current so that the planned irradiating particle count for the irradiation spot before the scan shift and the planned irradiating particle count for the irradiation spot after the scan shift have always values larger than half the irradiating particle count during the scan shift.

4. The particle beam scanning irradiation system of claim 1, further including a sixth step of calculating, when the particle beam moves with a blank shift, a distance between an irradiation spot before the blank shift and an irradiation spot after the blank from a shift path between the irradiation spots.

5. The particle beam scanning irradiation system of claim 4, further including a seventh step of subtracting one-nth of an irradiating particle count during the blank shift, from an irradiating particle count, for each irradiation spot being along the blank shift path,
by comparing the blank shift distance calculated in the sixth step with the scan shift distance and by determining a number (n) of blank spots among the blank shift distance.

* * * * *